United States Patent
Kowshik et al.

(10) Patent No.: US 12,011,241 B2
(45) Date of Patent: *Jun. 18, 2024

(54) FLEXIBLE INSTRUMENT WITH GROOVED STEERABLE TUBE

(71) Applicant: INTUITIVE SURGICAL OPERATIONS, INC., Sunnyvale, CA (US)

(72) Inventors: Anoop B. Kowshik, Saratoga, CA (US); Stephen J. Blumenkranz, Los Altos, CA (US); Carolyn M. Fenech, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1066 days.

This patent is subject to a terminal disclaimer.

(21) Appl. No.: 16/877,760

(22) Filed: May 19, 2020

(65) Prior Publication Data
US 2020/0345436 A1 Nov. 5, 2020

Related U.S. Application Data

(63) Continuation of application No. 15/031,310, filed as application No. PCT/US2014/062160 on Oct. 24, 2014, now Pat. No. 10,716,637.

(Continued)

(51) Int. Cl.
*A61B 34/00* (2016.01)
*A61B 17/00* (2006.01)
(Continued)

(52) U.S. Cl.
CPC ............ *A61B 34/35* (2016.02); *A61B 34/30* (2016.02); *A61B 34/71* (2016.02);
(Continued)

(58) Field of Classification Search
CPC ........ A61B 2017/003; A61B 2034/301; A61B 34/71; A61M 2025/0166; A61M 25/0138; A61M 25/0147
See application file for complete search history.

(56) References Cited

U.S. PATENT DOCUMENTS 5,251,611 A  10/1993  Zehel et al.
5,386,828 A   2/1995  Owens et al.
(Continued)

FOREIGN PATENT DOCUMENTS

EP  1679094 A1  7/2006
EP  1690564 A1  8/2006
(Continued)

OTHER PUBLICATIONS

<Span style="font-family: calibri;">Extended European Search Report for Application No. 14855614.5, dated Apr. 7, 2017, 9 pages.
(Continued)

*Primary Examiner* — Christine H Matthews
(74) *Attorney, Agent, or Firm* — Haynes & Boone, LLP

(57) ABSTRACT

A minimally invasive medical instrument comprises an elongate flexible body comprising a proximal portion, a distal portion, a transition portion between the proximal portion and the distal portion, and an inner sheath extending at least within the proximal portion. The inner sheath comprises a plurality of conduits extending through a wall of the inner sheath. A distal end of each conduit terminates at the transition portion. The flexible body further comprises a steerable tube extending within the distal portion. The steerable tube comprises a plurality of grooves in a wall of the steerable tube. The medical instrument further comprises at least one tendon extending from the proximal portion into the distal portion of the flexible body. In the proximal portion, the tendon extends through at least one conduit of the plurality of conduits. In the distal portion, the tendon (Continued)

extends within at least one groove of the plurality of grooves.

20 Claims, 11 Drawing Sheets

Related U.S. Application Data

(60) Provisional application No. 61/895,761, filed on Oct. 25, 2013.

(51) Int. Cl.
*A61B 34/30* (2016.01)
*A61B 34/35* (2016.01)
*A61B 34/20* (2016.01)
*A61M 25/01* (2006.01)

(52) U.S. Cl.
CPC ............... *A61B 2017/003* (2013.01); *A61B 2017/00309* (2013.01); *A61B 2034/2051* (2016.02); *A61B 2034/2061* (2016.02); *A61B 2034/301* (2016.02); *A61M 25/0138* (2013.01); *A61M 25/0147* (2013.01); *A61M 2025/0166* (2013.01)

(56) References Cited

U.S. PATENT DOCUMENTS

| | | | |
|---|---|---|---|
| 5,438,975 A | 8/1995 | Miyagi et al. | |
| 6,380,732 B1 | 4/2002 | Gilboa | |
| 6,389,187 B1 | 5/2002 | Greenaway et al. | |
| 6,450,948 B1 | 9/2002 | Matsuura et al. | |
| 6,623,448 B2 | 9/2003 | Slater | |
| 7,772,541 B2 | 8/2010 | Froggatt et al. | |
| 7,781,724 B2 | 8/2010 | Childers et al. | |
| 8,273,285 B2 | 9/2012 | Wilkowske et al. | |
| 8,900,131 B2 | 12/2014 | Chopra et al. | |
| 9,033,917 B2 | 5/2015 | Magana et al. | |
| 9,254,123 B2 | 2/2016 | Alvarez et al. | |
| 10,716,637 B2 | 7/2020 | Kowshik et al. | |
| 11,007,026 B2 | 5/2021 | Kowshik | |
| 2003/0097128 A1 | 5/2003 | Hayzelden | |
| 2005/0154261 A1 | 7/2005 | Ohline et al. | |
| 2006/0013523 A1 | 1/2006 | Childers et al. | |
| 2006/0151923 A1 | 7/2006 | Wilkowske et al. | |
| 2007/0156019 A1 | 7/2007 | Larkin et al. | |
| 2007/0161857 A1 | 7/2007 | Durant et al. | |
| 2009/0062606 A1 | 3/2009 | Ueda et al. | |
| 2009/0099420 A1 | 4/2009 | Woodley et al. | |
| 2009/0137875 A1 | 5/2009 | Kitagawa et al. | |
| 2009/0182200 A1 | 7/2009 | Golden et al. | |
| 2009/0192495 A1 | 7/2009 | Ostrovsky et al. | |
| 2010/0168717 A1 | 7/2010 | Grasse et al. | |
| 2010/0280449 A1* | 11/2010 | Alvarez | A61B 34/71 606/1 |
| 2011/0004157 A1 | 1/2011 | Dewaele et al. | |
| 2011/0015648 A1 | 1/2011 | Alvarez et al. | |
| 2011/0237888 A1 | 9/2011 | Matsushita et al. | |
| 2011/0306836 A1 | 12/2011 | Ohline et al. | |
| 2013/0028554 A1 | 1/2013 | Wong et al. | |
| 2013/0096377 A1 | 4/2013 | Duindam et al. | |
| 2013/0096385 A1 | 4/2013 | Fenech et al. | |
| 2013/0274784 A1 | 10/2013 | Lenker et al. | |
| 2013/0300036 A1 | 11/2013 | Wilkowske et al. | |
| 2014/0088358 A1 | 3/2014 | Banik et al. | |
| 2016/0256230 A1 | 9/2016 | Kowshik et al. | |
| 2016/0270870 A1 | 9/2016 | Kowshik et al. | |
| 2021/0212783 A1 | 7/2021 | Kowshik | |

FOREIGN PATENT DOCUMENTS

| | | |
|---|---|---|
| JP | 2009056054 A | 3/2009 |
| JP | 2012213505 A | 11/2012 |
| WO | WO-2007120329 A2 | 10/2007 |

OTHER PUBLICATIONS

Extended European Search Report for Application No. 14856191.3, dated Apr. 7, 2017, 10 pages.
Extended European Search Report for Application No. EP18169329.2, dated Aug. 16, 2018, 7 pages.
Extended European Search Report for Application No. EP20151031.0 dated Feb. 11, 2020, 11 pages.
International Preliminary Report on Patentability for Application No. PCT/US14/62160, dated May 6, 2016, 13 pages.
International Preliminary Report on Patentability for Application No. PCT/US2014/062188, dated May 6, 2016, 12 pages.
International Search Report and Written Opinion for Application No. PCT/US14/62160, dated Jan. 28, 2015, 16 pages.
International Search Report and Written Opinion for Application No. PCT/US14/62188, dated Feb. 4, 2015, 15 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

FLEXIBLE INSTRUMENT WITH GROOVED STEERABLE TUBE

CROSS-REFERENCE TO RELATED APPLICATIONS

This patent application is a continuation of U.S. patent application Ser. No. 15/031,310, filed Apr. 22, 2016, which is the U.S. national phase of International Application No. PCT/US2014/062160, filed Oct. 24, 2014, which designated the U.S. and claims priority to and the benefit of the filing date of U.S. Provisional Application No. 61/895,761, entitled "FLEXIBLE INSTRUMENT WITH GROOVED STEERABLE TUBE," filed Oct. 25, 2013, all of which are incorporated by reference herein in their entirety.

FIELD

The present disclosure is directed to systems and methods for navigating a patient anatomy to conduct a minimally invasive procedure, and more particularly to apparatus and methods for steering a low-profile, flexible interventional instrument into a patient anatomy.

BACKGROUND

Minimally invasive medical techniques are intended to reduce the amount of tissue that is damaged during interventional procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. To reach the target tissue location, a minimally invasive interventional instrument may navigate natural or surgically created passageways in anatomical systems such as the lungs, the colon, the intestines, the kidneys, the heart, the circulatory system, or the like. Some minimally invasive medical instruments may be teleoperated or otherwise computer-assisted. Telerobotic interventional instruments may be used to navigate through the patient anatomy, and such instruments need to be small enough to physically fit within those anatomical lumens. Manufacturing a flexible telerobotic instrument that is sized to contain the mechanical structures suitable for remote or telerobotic operation and that has an outer diameter that is sufficiently small to navigate such small passageways can be challenging. Improved devices and systems are needed for telerobotic surgical instruments configured for insertion into anatomical or surgically-created passageways.

SUMMARY

The embodiments of the invention are summarized by the claims that follow the description.

In one exemplary aspect, the present disclosure is directed to a minimally invasive surgical or diagnostic instrument comprising an elongate flexible body, a plurality of conduits, a plurality of tendons, and a steerable tube. In one aspect, the elongate flexible body includes a proximal portion and a distal portion. In one aspect, each conduit includes a lumen and extends through the proximal portion of the elongate flexible body. In one aspect, the plurality of tendons extends from the proximal portion to the distal portion of the elongate flexible body, with each tendon being actuatable to bend the steerable tube. In one aspect, the steerable tube extends within the distal portion of the elongate flexible body, and includes an inner surface, an outer surface, and a wall having a thickness extending between the inner surface and the outer surface. In one aspect, the steerable tube includes a plurality of channels in the wall configured to receive the tendons.

In another exemplary aspect, the present disclosure is directed to a minimally invasive surgical or diagnostic system comprising an actuator, an elongate flexible body, a steerable tube, a plurality of conduits, and a plurality of actuation tendons. In one aspect, the elongate flexible body includes a proximal portion, a distal portion, and a flexible sheath defining a central lumen and extending through the proximal portion. In one aspect, the steerable tube is coupled to the distal portion of the elongate flexible body, and includes an inner surface, an outer surface, a wall having a thickness extending between the inner surface and the outer surface. In one aspect, the steerable tube includes a plurality of channels in the wall configured to receive the conduits. In one aspect, the plurality of conduits is embedded within the flexible sheath, and each conduit includes a lumen and extends through the flexible inner sheath. In one aspect, at least one conduit of the plurality of conduits extends from the proximal portion through the steerable tube in the distal portion. In one aspect, each actuation tendon is fixed at a proximal end relative to the actuator and extends through the lumen of one of the plurality of conduits into the wall of the steerable tube. In one aspect, the plurality of actuation tendons is actuatable to bend the steerable tube.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 6a illustrates a perspective view of an exemplary steerable tube according to one embodiment of the present disclosure.

FIG. 6b illustrates a detailed perspective view of a portion of the exemplary steerable tube shown in FIG. 6a.

DETAILED DESCRIPTION

Figure 1:
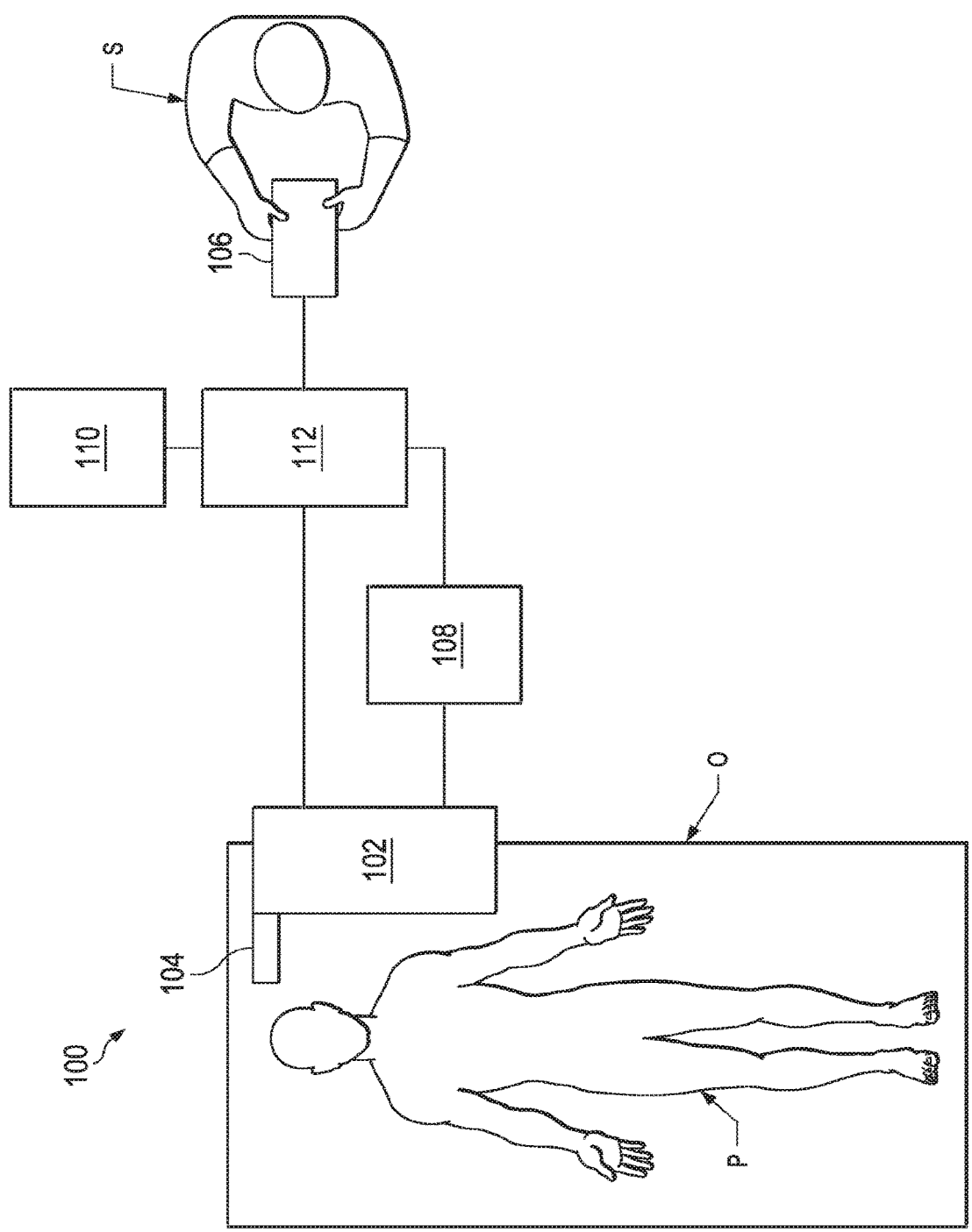
FIG. 1 illustrates a telerobotic interventional system in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates.

In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an elongated object.

It will be appreciated that the terms "proximal" and "distal" are used herein with reference to a clinician manipulating an end of an instrument extending from the clinician to a surgical or diagnostic site. The term "proximal" refers to the portion of the instrument closer to the clinician, and the term "distal" refers to the portion of the instrument further away from the clinician and closer to the surgical or diagnostic site. For conciseness and clarity, spatial terms such as "horizontal," "vertical," "above," and "below" may be used herein with respect to the drawings. However, surgical and diagnostic instruments are used in many orientations and positions, and there terms are not intended to be limiting and absolute.

The present disclosure relates generally to steerable tubes used in the operation of articulating devices. In some instances, embodiments of the present disclosure are configured to be part of a telerobotic system. Those of skill in the art will realize that the steerable tubes disclosed herein may be utilized in similar (e.g., non-telerobotic) applications requiring a steerable distal tip.

The steerable tubes disclosed herein are formed of a flexible material and are configured to carry control cables or tendons. The walls of the steerable tubes disclosed herein include grooves or channels that are shaped and configured to carry control cables/tendons. By allowing the control cables/tendons to rest within these grooves or channels, the steerable tubes disclosed herein allow for an increase in the thickness of the steerable tube without undesirably increasing an outer diameter of the steerable portion of the articulating device or undesirably reducing an inner luminal diameter of the articulating device. In some embodiments, the grooves or channels are intelligently aligned relative to the articulation cut-out features of the steerable tube to maximize the mechanical performance of the steerable tube. Thus, the steerable tubes disclosed herein may improve the durability and performance of steerable portions of articulating devices, and may increase the range of suitable applications for articulating devices utilizing such steerable tubes.

According to various embodiments, medical procedures, such as biopsy procedures, may be performed using a teleoperational system to guide instrument delivery. Referring to FIG. 1 of the drawings, a teleoperational medical system for use in, for example, medical procedures including diagnostic, therapeutic, or surgical procedures, is generally indicated by the reference numeral 100. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1, the teleoperational medical system 100 generally includes a teleoperational assembly 102 mounted to or near an operating table O on which a patient P is positioned. A medical instrument system 104 is operably coupled to the teleoperational assembly 102. An operator input system 106 allows a surgeon or other type of clinician S to view images of or representing the surgical site and to control the operation of the medical instrument 104.

The operator input system 106 may be located at a surgeon's console, which is usually located in the same room as operating table O. It should be understood, however, that the surgeon S can be located in a different room or a completely different building from the patient P. Operator input system 106 generally includes one or more control device(s) for controlling the medical instrument system 104. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device (s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of motors that drive inputs on the medical instrument system 104. These motors move in response to commands from the control system (e.g., control system 112). The motors include drive systems which when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes a sensor system 108 with one or more sub-systems for receiving information about the instruments of the teleoperational assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

Alternatively or additionally, display system 110 may present images of the surgical site recorded and/or imaged preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and the like. The presented preoperative or intraoperative images may include two-dimensional, three-dimensional, or four-dimensional (including e.g., time based or velocity based information) images and associated image data sets for reproducing the images.

In some embodiments, the display system 110 may display a virtual visualization image in which the actual location of the medical instrument is registered (e.g., dynamically referenced) with preoperative or concurrent images to present the surgeon with a virtual image of the internal surgical site at the location of the tip of the medical instrument.

In other embodiments, the display system 110 may display a virtual visualization image in which the actual location of the medical instrument is registered with prior images (including preoperatively recorded images) or concurrent images to present the surgeon with a virtual image of a medical instrument at the surgical site. An image of a portion of the medical instrument system 104 may be superimposed on the virtual image to assist the surgeon controlling the medical instrument. The teleoperational medical system 100 also includes a control system 112. The control system 112 includes at least one memory and at least one processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104. Virtual navigation using the virtual visualization system is based upon reference to an acquired dataset associated with the three dimensional structure of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intra-operatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomical Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
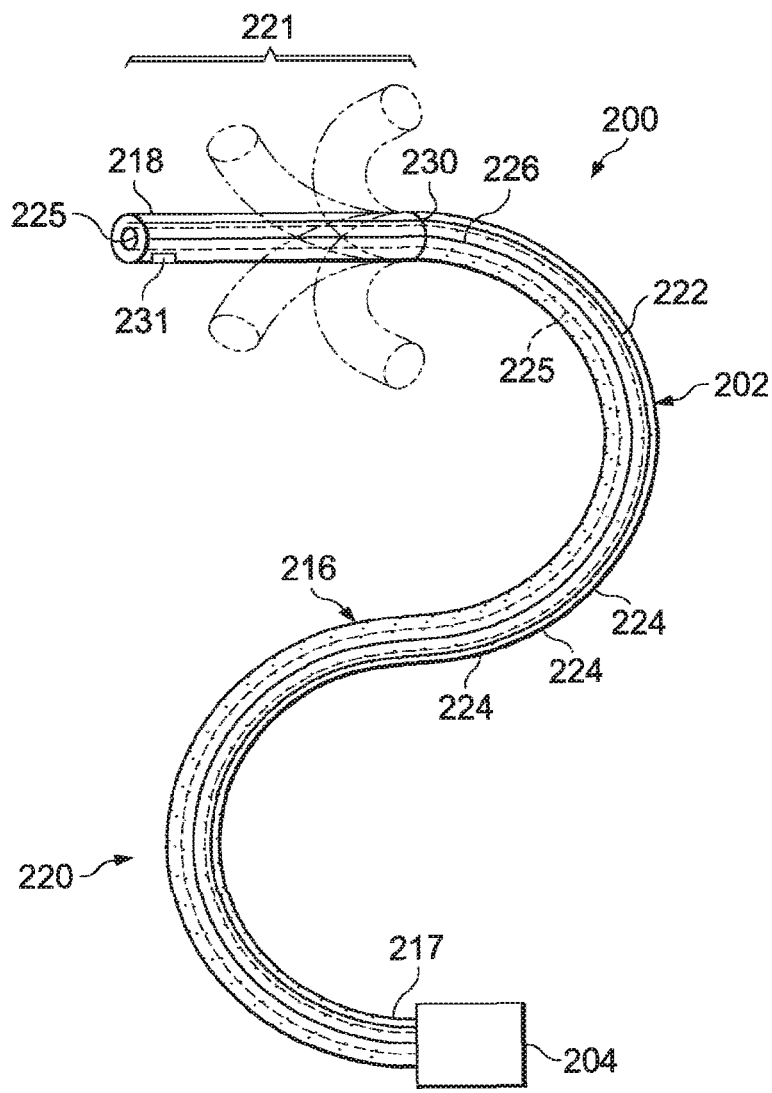
FIG. 2 illustrates an interventional instrument system in accordance with an embodiment of the present disclosure.

FIG. 2 illustrates an interventional instrument system 200 which may be used as the interventional instrument system 104 of the telerobotic interventional system 100. Alternatively, the interventional instrument system 200 may be used for non-robotic exploratory procedures or in procedures involving traditional manually operated interventional instruments, such as endoscopy. In various embodiments, the interventional instrument system 200 may include a flexible bronchial instrument, such as a bronchoscope or bronchial catheter for use in examination, diagnosis, biopsy, or treatment of a lung. The system is also suited for navigation and treatment of other tissues, via natural or surgically created connected passageways, in any of a variety of anatomical systems including the colon, the intestines, the kidneys, the brain, the heart, the circulatory system, or the like.

The instrument system 200 includes a catheter system 202 coupled to an instrument body 204. The catheter system 202 includes an elongated flexible body 216 having a proximal end 217 and a distal end or tip portion 218. A distal portion 221 extends between the distal end 218 and a transition section 230. A proximal portion 220 extends between the transition section 230 and the proximal end 217. In one embodiment, the flexible body 216 has an approximately 3 mm outer diameter. Other flexible body outer diameters may be larger or smaller. In some embodiments, the flexible body outer diameter tapers from the proximal end 217 to the distal end 218. In other embodiments, the flexible body outer diameter at the proximal end 217 is greater than the flexible body outer diameter at the distal end 218. In some embodiments, the flexible body outer diameter is substantially unchanged throughout the proximal portion 220. In some embodiments, the flexible body outer diameter is substantially unchanged throughout the distal portion 221. In other embodiments, the flexible body outer diameter may taper throughout the proximal portion 220 and/or the distal portion 221. In other embodiments, there can be an abrupt change or stop in the flexible body 216 at the transition section 230 from a larger outer diameter of the proximal portion 220 to a smaller diameter of the distal portion 221.

The catheter system 202 may optionally include a shape sensor 222 for determining the position, orientation, speed, pose, and/or shape of the catheter tip at distal end 218 and/or of one or more segments 224 along the body 216. The entire length of the body 216 between the distal end 218 and the proximal end 217 may be effectively divided into the segments 224. If the instrument system 200 is an interventional instrument system 104 of the telerobotic interventional system 100, the shape sensor 222 may be a component of the sensor system 108. If the instrument system 200 is manually operated or otherwise used for non-robotic procedures, the shape sensor 222 may be coupled to a tracking system that interrogates the shape sensor and processes the received shape data.

The shape sensor system 222 may include an optical fiber aligned with the flexible catheter body 216 (e.g., provided within an interior conduit (not shown) or mounted externally). The optical fiber of the shape sensor system 222 may form a fiber optic bend sensor for determining the shape of at least a portion of the catheter system 202. Various systems and methods for monitoring the shape and relative position of an optical fiber in three dimensions are described in U.S. patent application Ser. No. 11/180,389, filed Jul., 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the catheter may be determined using other techniques.

More specifically, light passing through the optical fiber is processed to detect the shape of the catheter system 202 and for utilizing that information to assist in surgical procedures. The sensor system (e.g. sensor system 108 or another type of tracking system as described in HG. 3) may include an interrogation system for generating and detecting the light used for determining the shape of the catheter system 202. This information, in turn, in can be used to determine other related variables, such as velocity and acceleration of the parts of an interventional instrument.

The flexible catheter body 216 includes a lumen 225 sized and shaped to receive an auxiliary tool 226. Auxiliary tools may include, for example, image capture probes, biopsy devices, laser ablation fibers, or other surgical, diagnostic, or therapeutic tools. Auxiliary tools may include end effectors having a single working member such as a scalpel, a blade, an optical fiber, or an electrode. Other end effectors may include pair or plurality of working members such as forceps, graspers, scissors, or clip appliers, for example. Examples of electrically activated end effectors include electrosurgical electrodes, transducers, sensors, and the like.

In various embodiments, the auxiliary tool 226 may be an image capture probe including a tip portion with a stereoscopic or monoscopic camera disposed near the distal end 218 of the flexible catheter body 216 for capturing images (including video images) that are processed for display. The image capture probe may include a cable coupled to the camera for transmitting the captured image data. Alternatively, the image capture instrument may be a fiber-optic bundle, such as a fiberscope, that couples to the imaging system. The image capture instrument may be single or multi-spectral, for example capturing image data in the visible spectrum, or capturing image data in the visible and infrared or ultraviolet spectrums.

The catheter system 202 may optionally include a position sensor system 231 (e.g., an electromagnetic (EM) sensor system) which may be disabled by an operator or an automated system (e.g., a function of the control system 112) if it becomes unreliable due to, for example, magnetic interference from other equipment in the surgical suite or if other navigation tracking systems are more reliable. The position sensor system 231 may be an EM sensor system that includes one or more conductive coils that may be subjected to an externally generated electromagnetic field. Each coil of the EM sensor system 231 then produces an induced electrical signal having characteristics that depend on the position and orientation of the coil relative to the externally generated electromagnetic field. In one embodiment, the EM sensor system may be configured and positioned to measure six degrees of freedom ("6-DOF"), e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

The flexible catheter body 216 may also house cables, linkages, or other steering controls (not shown in FIG. 2) that extend between the instrument body 204 and the distal end 218 to controllably bend or turn the distal portion 221 as shown for example by the dotted line versions of the distal portion. In some embodiments, the flexible body 216 can define one or more additional lumens through which interventional instruments, cables, linkages, and/or other steering controls (such as, by way of non-limiting example, coil pipes and tendons) may extend.

In embodiments in which the instrument system 200 is actuated by a telerobotic assembly, the instrument body 204 may include drive inputs that couple to motorized drive elements of the telerobotic assembly. In embodiments in which the instrument system 200 is manually operated, the instrument body 204 may include gripping features, manual actuators, and other components for manually controlling the motion of the instrument system. The catheter system may be steerable or, alternatively, may be non-steerable with no integrated mechanism for operator control of the instrument bending. In some embodiments, the proximal portion 220 is configured to passively deflect in response to forces acting upon the flexible body, and the distal portion 221 is configured to actively articulate in response to the telerobotic assembly and/or control signals from the instrument body 204.

Figure 3:
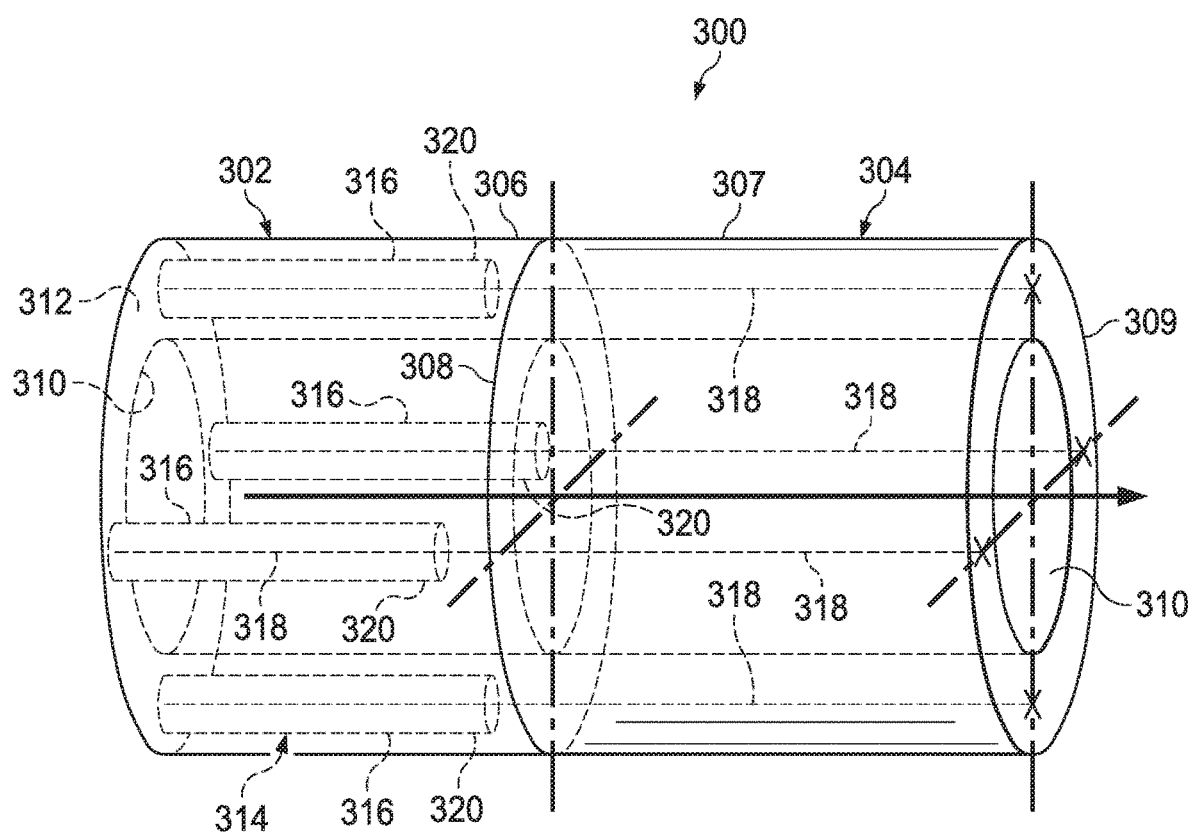
FIG. 3 illustrates a steerable portion of a catheter system, showing relative positions of various elements that enable articulation of the system in accordance with an embodiment of the present disclosure.

FIG. 3 illustrates a portion of a catheter system 300 having a proximal portion 302, a distal portion 304, and a transition section 306 disposed therebetween. The catheter system 300 may be the same as the catheter system 202 described above in relation to FIG. 2. The proximal portion 302 may be the same as a distal-most segment 224 of the proximal portion 220 and the distal portion 304 may be the same as a proximal-most segment 224 of the distal portion 221 of the catheter system 202. In some embodiments, the transition section 306 is the same as the transition section 230 shown between the proximal portion 220 and the distal portion 221 shown in FIG. 2. In the pictured embodiment, the distal portion 304 includes a proximal-most steerable segment 307. The steerable segment 307 includes a proximal end 308 and a distal end 309.

A lumen 310 (e.g., lumen 225) extends centrally through the proximal portion 302, the transition section 306 and distal portion 304 of the catheter system 300. The catheter system 300 includes a flexible wall 312 with layered wall components (see FIGS. 4 and 5) that are omitted from the illustration of FIG. 3 for the sake of clarity.

Bowden cables 314 extend down the length of a catheter flexible body (e.g., flexible body 216) of the catheter system 300 to the distal portion 304. In this embodiment, the Bowden cables 314 extend entirely within or at least partially within the wall 312. The Bowden cables 314 comprise conduits or coil pipes 316 through which control wires or tendons 318 extend. The coil pipes 316 house the tendons 318 along the length of the flexible body, and the tendons 318 can slide longitudinally within the coil pipes 316. The coil pipes 316 terminate at the transition section 306, proximal to the steerable segment 307 within the distal portion 304. The tendons 318 extend out of the coil pipes 316 at the transition section 306, enter the proximal end 308, extend through the steerable segment 307, and attach to the distal end 309.

In the pictured embodiment, four coil pipes 316 are arranged circumferentially in the wall 312 around the lumen 310. Other embodiments may include any number of coil pipes 316 arranged in any of a variety of symmetrical or asymmetrical patterns within the wall 312.

In the pictured embodiment, the coil pipes 316 terminate within the flexible wall 312 of the steerable segment 307 in approximately a common plane perpendicular to the lumen 310. As shown in FIG. 3, the coil pipes 316 terminate in a non-discrete portion of the wall 312 where the coil pipes 316 are embedded or anchored to the wall 312 (or similar flexible sheath-like structure). In the pictured embodiment, a distal end 320 of each coil pipe 316 is directly secured to the wall 312 proximal to the steerable segment 307. In some embodiments, the coil pipes 316 may have a surface treatment to aid in fixation to the wall 312. In some embodiments, the distal end 320 of each coil pipe 316 may be secured to the wall 312 via, by way of non-limiting example, an adhesive or melting. In the pictured embodiment, the distal ends 320 of the coil pipes 316 are not anchored to any discrete element, such as a rigid ring, within the flexible wall 312 or catheter system 300. Rather, each coil pipe 316 terminates within and is affixed to the wall 312 at a position proximal to whichever steerable segment (e.g., the steerable segment 307) is configured to be steered by the tendon 318 carried within the particular coil pipe 316. In other embodiments, the distal ends 320 of the coil pipes 316 may be anchored to a discrete element within the flexible wall 312 of the catheter system 300. The tendons 318 continue past the distal ends 320 of the coil pipes 316 to extend through the steerable segment 307 and terminate at the distal end 309 of the steerable segment 307. For additional structural support, an additional wire coil may be wrapped around each of the coil pipes 316 within the coil pipe winds.

Although the coil pipes 316 in the pictured embodiment terminate in a common plane within the proximal portion 302, it should be understood that an individual coil pipe 316 could extend into any length of the flexible body 216 with the coil pipes 316 terminating at different lengths (i.e., not in a common plane). For example, in some embodiments, at least one of the coil pipes 316 extends the entire length or substantially the entire length of the flexible body (e.g., to a distal-most steerable segment within the distal portion 304). In other embodiments, the coil pipes 316 extend only partially along the length of the flexible body.

A proximal end of each tendon 318 is coupled to an actuator (not shown). In some embodiments, the actuator may be disposed within the instrument body 204 shown in FIG. 2. The tension applied to a tendon 318 by the actuator is isolated to the particular segment 307 through the use of the coil pipes 316. These Bowden cables 314 can be actuated remotely and can be used to selectively apply force to and articulate the steerable segment 307. The tendons 318 may be made from any of a variety of materials, including without limitation, stainless steel, titanium, Nitinol, ultra-high molecular weight polyethylene, and any other suitable material known to the skilled artisan. In some embodiments, the Bowden cables 314 are substantially similar in construct and in operation to the cables disclosed in U.S. Patent Application No. 2009/0099420 A1, entitled "System for Managing Bowden Cables in Articulating Instruments," filed Oct. 11, 2007, and published on Apr. 16, 2009, which is incorporated by reference herein in its entirety. As mentioned above, it is appreciated by a person skilled the art that additional coil pipes may travel through or around the steerable segment 307 to terminate at more distal segments of the proximal or distal portion of the catheter.

Figure 4:
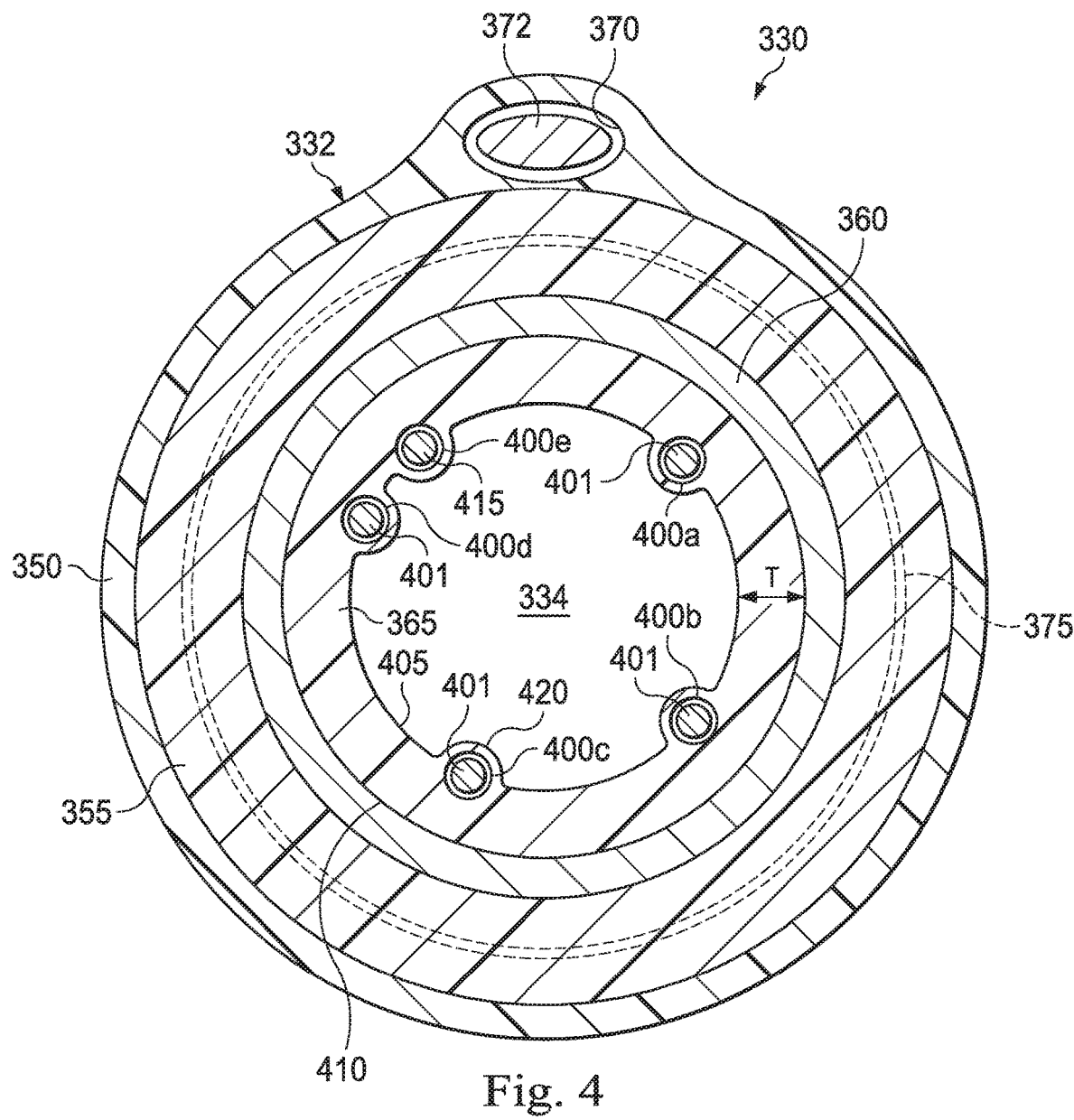
FIG. 4 illustrates a cross-sectional view of an exemplary proximal portion of the instrument system shown in FIG. 2 in accordance with an embodiment of the present disclosure.

FIG. 4 illustrates a cross-sectional view of a proximal portion 330 (e.g., the proximal portion 220 of the exemplary catheter system 202 pictured in FIG. 2). At the proximal portion 330, a flexible body 332 comprises a multi-layered, hollow cylindrical tube defining a lumen 334. In the proximal portion 330, the flexible body 332 comprises an outer sheath 350, a support layer 355, a coil layer 360, and an inner sheath 365, each of which is disposed concentrically and co-axially about the lumen 334. The outer sheath 350 includes a lumen 370 configured to carry at least a portion of a position sensor system 372 (e.g., an EM sensor wire and/or associated positional signal wires). In the pictured embodiment, the support layer 355 includes an embedded support component 375, which assists in maintaining the patency of the lumen 334 (and any other lumens) during articulation of the elongate flexible body 332. In some embodiments, the support component 375 comprises a tubular braided element such as, by way of non-limiting example, a polyimide braid. The support component may resist radial expansion and/or increase torsional stiffness. The support component 375 is sandwiched within the support layer 355, which may be fabricated of two separately extruded lengths of flexible tubing that may be bonded to one another and/or the support component 375. The coil layer 360 may also assist in maintaining the patency of the lumen 334 (and any other lumens) during articulation of the elongate flexible body 332. In some embodiments, the coil layer 360 includes a wound element having either an open pitch or a closed pitch. In other embodiments, the coil layer 360 includes a woven or braided element. Other embodiments may lack a support layer 355 and/or a coil layer 360. Other embodiments may include any number or arrangement of support layers and/or coil layers between the outer sheath 350 and the inner sheath 365.

The inner sheath 365 comprises a length of flexible tubing with a thickness T extending from an inner surface 405 to an outer surface 410. The inner sheath includes five conduits, includes four conduits 400a, 400b, 400c, and 400d configured to carry the tendons 401, and a sensor conduit 400e configured to carry a sensor element 415. In some embodiments, the conduits 400a-e comprise a narrow ribbon of material shaped into a cylindrical coil or coil pipe (e.g., the coil pipe 316). The coiled nature of such a conduit may allow it to perform well under tension and compression. Each conduit 400a-e may extend within a preformed channel through the inner sheath or may be embedded in the inner sheath as the inner sheath is extruded around the conduit. The conduits 400 may be arranged asymmetrically about the inner sheath 365. In other embodiments, the inner sheath 365 may contain any number, type, and arrangement of conduits 400, depending upon the application and structure of the instrument system 200.

In the embodiment of FIG. 4, the conduits 400 are disposed within the inner sheath 365 closer to the inner surface 405 than the outer surface 410 of inner sheath 365, creating protrusions 420. In the pictured embodiment, the protrusions 420 are intraluminal protrusions. In other words, the protrusions 420 extend into the lumen 334. In other embodiments, the conduits 400 may be disposed within the inner sheath 365 closer to the outer surface 410 than shown in the pictured embodiment, and the protrusions 420 may be smaller than shown or on the outer surface 410 or nonexistent.

In some embodiments, the inner sheath 365, the support layer 355, and/or the support component 375 are configured to maintain the conduits 400 in a substantially known radial position through the length of or at least a portion of the length of the flexible body 216. This may allow for a reliable correlation between the shape and orientation of sensory fibers extending through the flexible body 332 (e.g., the sensor element 415 and/or the position sensor system 231) and the shape and orientation of the flexible body 332. In some embodiments, the radial position of the conduits 400 varies, along the length of the flexible body 332, relative to the inner surface 405 and the outer surface 410. For example, in some embodiments, the conduits 400 may shift closer to the outer surface 410 as the conduits 400 extend distally through the flexible body 332 toward the distal portion.

Tendons 401 (e.g., tendons 318) are disposed coaxially within the conduits 400a, 400b, 400c, and 400d. In some embodiments, the conduits 400a-e are configured to maintain the patency or openness of the flexible body lumen 334 and minimize friction such that the tendon 401 can slide freely or float within the conduit. In some embodiments, the conduits 400a-e are configured to provide reliable positioning of the tendons 318 along the length of the flexible body 332.

In this embodiment, the conduits 400a-e extend within the inner sheath 365 along substantially the entire length of the conduits 400a-e. In some prior art catheter systems, steering cables (e.g., Bowden cables) extend through the catheter lumen without attachment to the lumen wall or with only periodic anchor locations or cable termination locations on the catheter wall. In other prior art systems, steering cables were attached to periodically to an outer surface of the catheter. In both of these prior art configurations, the steering cables would separate from the catheter wall, creating a straight line between attachment points (a situation commonly known as "cheese-wiring"). In the embodiment of FIG. 4, the inner sheath 365 captures the conduits 400 preventing separation from the catheter wall. As will be described further for FIGS. 10 and 11, embedding the conduits entirely or at partially within the wall of the flexible body 332, without the use of rigid rings for conduit anchoring or termination may allow the flexible body to resist forming sharp bends (at or near the site of the rigid rings) when used in tortuous anatomical passageways.

The conduits 400 may be constructed of any number of a variety of flexible materials, including without limitation, nylon, polyimide, PTFE, Pebax, and any other suitable material known to the skilled artisan. The conduits 400 may be constructed with a coil or braided structure. The inner sheath 365 may be constructed of any number of a variety of flexible materials, including without limitation, polyurethane, FEP, Pebax, and any other suitable material known to the skilled artisan.

Figure 5:
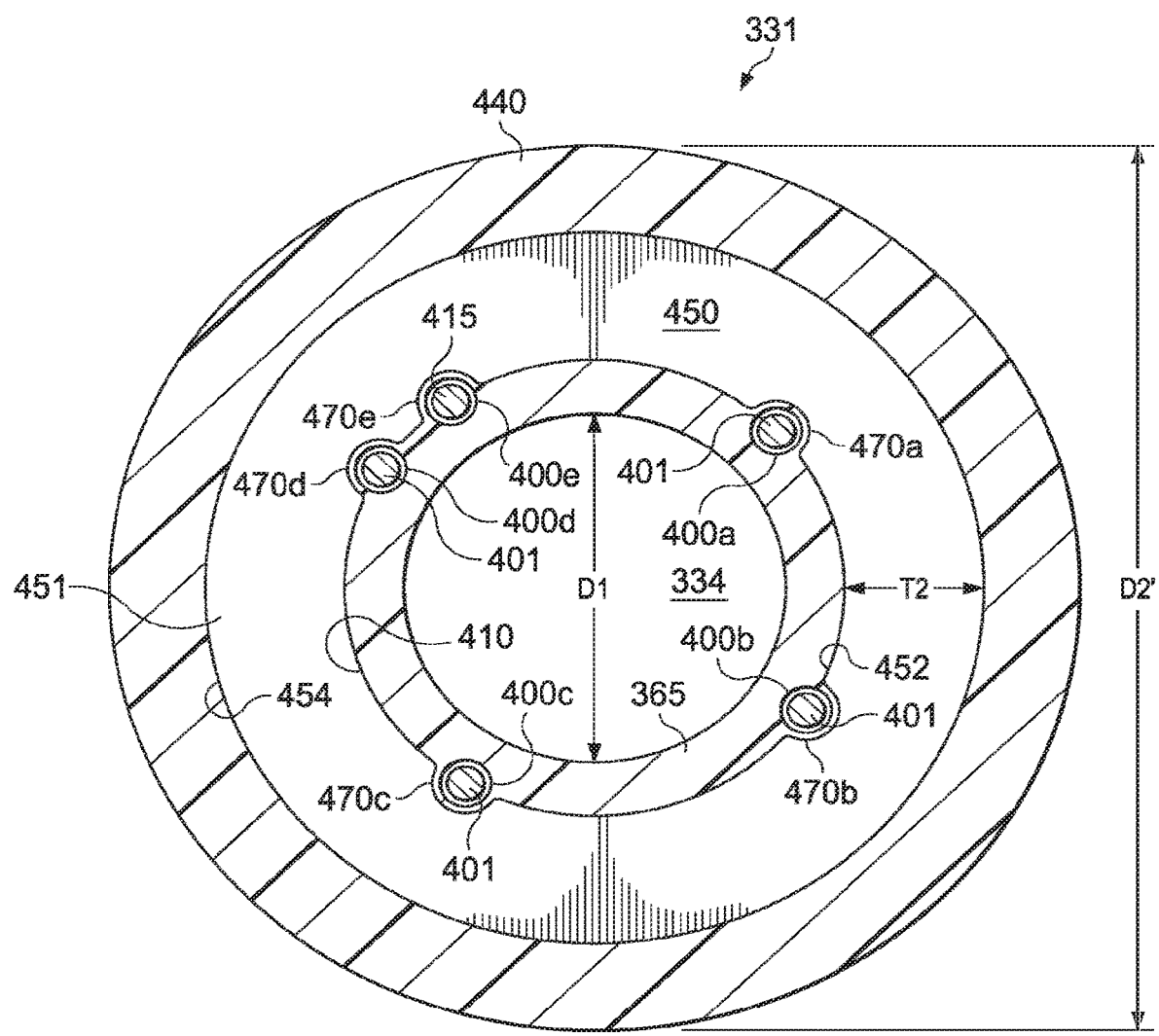
FIG. 5 illustrates a cross-sectional view of an exemplary distal portion of the instrument system shown in FIG. 2 in accordance with an embodiment of the present disclosure.

FIG. 5 illustrates a cross-sectional view of a distal portion 331 (e.g., the distal portion 221 of the exemplary catheter system 202 pictured in FIG. 2). At the distal portion 331, the flexible body 332 comprises a multi-layered, hollow cylindrical tube defining the lumen 334. The flexible body 332 in the distal portion 331 comprises an outer sheath 440, a steerable tube 450, and the inner sheath 365, each of which is disposed concentrically and co-axially about the lumen 334. In some embodiments, the outer sheath 440 is the same as or continuous with the outer sheath 350 described above in relation to FIG. 4. In the pictured embodiment, the outer sheath 440 encases the steerable tube 450, and the steerable tube 450 concentrically surrounds the inner sheath 365, which defines the lumen 334. The outer sheath 440 may be configured to support and constrain the steerable tube 450 as it bends or flexes. In some embodiments, the outer sheath 440 is configured to bend and flex with the motion of the steerable tube 450 without unduly restricting the motion of the steerable tube 450.

As described above in relation to FIG. 4, the inner sheath 365 includes the five conduits, including the four tendon conduits 400a, 400b, 400c, and 400d configured to carry the tendons 401, and the sensor conduit 400e configured to carry the sensor clement 415. In the distal portion 331, the conduits 400a-e are closer to the outer surface 410 of the inner sheath and the protrusions into the lumen 334 are eliminated. In various alternative embodiments, all or some of the conduits may terminate at the distal end of the proximal portion (e.g. at the transition section 230 in FIG. 2) such that only the tendons, not the conduits, extend into the distal portion of the catheter. Some alternative embodiments may lack the inner sheath 365 in the distal portion 331 of the catheter, and the conduits 400a-e may be captured by the steerable tube 450 as described in further detail below.

The steerable tube 450 comprises a tubular member disposed between the inner sheath 365 and the outer sheath 440. The steerable tube 450 has a wall 451 and a wall thickness T2 extending between an inner surface 452 and an outer surface 454 of the wall 451. The distal portion 331 has an inner diameter D1 that spans the lumen 334, and an outer diameter D2 that spans the outer sheath 440. The inner diameter D1 may range from 1.5 to 2.5 mm, and the outer diameter D2 may range from 2.5 to 4 mm. These measurements are provided for exemplary purposes only, and are not intended to be limiting. The steerable tube 450 is shaped and configured to maximize the axial stiffness in the constrained annular space between the inner sheath 365 and the outer sheath 440 while carrying the conduits 400 within indentations or grooves 470a-e, which are described further below.

Figure 6:
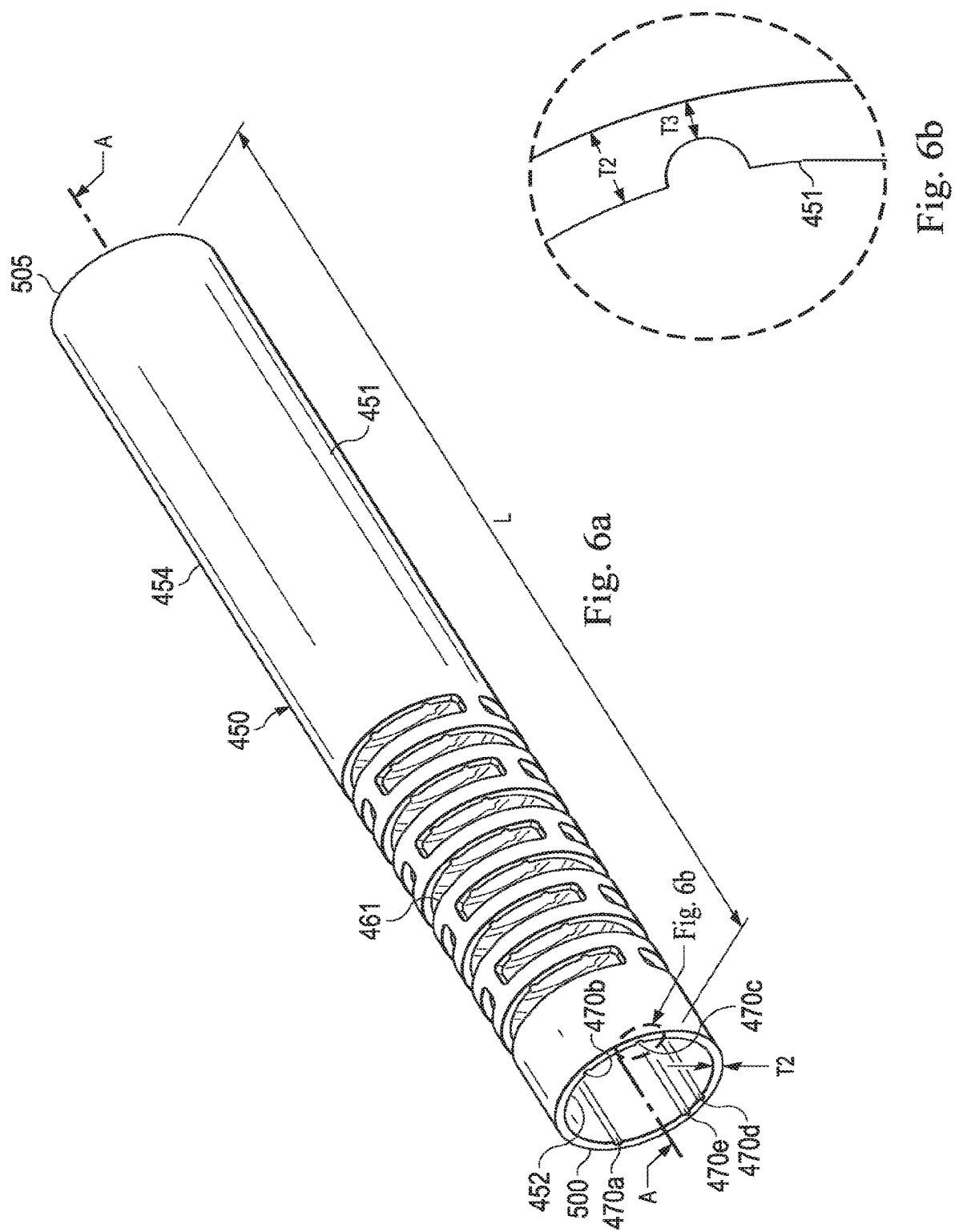

FIG. 6a illustrates a perspective view of the steerable tube 450 according to one embodiment of the present disclosure. In the embodiment pictured in FIG. 6a, the steerable tube 450 comprises a hollow, elongate, tubular member having a length L extending from a proximal end 500 to a distal end 505. In the pictured embodiment, the steerable tube 450 has a cylindrical shape in the non-flexed state and extends along a longitudinal axis AA.

The steerable tube 450 may include a plurality of cuts or cut-out features 461. The cut-out features 461 are formed with a pattern that provides an optimal balance of axial, bending, and torsional stiffness. In the pictured embodiment, the cut-out features are formed substantially perpendicular to the longitudinal axis AA. The cut-out features 461 allow the steerable tube 450 to bend in multiple dimensions. In some embodiments, the frequency and pattern of cuts in any given portion of the steerable tube 450 may determine the flexibility of that portion. In some embodiments, a higher spatial frequency of cuts may correspond to a higher flexibility. In the pictured embodiment, the cut-out features 461 only extend along a portion of the steerable tube 450. In other embodiments, the cut-out features may extend the entire length of the steerable tube 450, or along a different portion of the steerable tube 450. The cut-out features 461 illustrated in the drawings are merely exemplary, and are not intended to be limiting in number, type, arrangement, or shape. In various embodiments, the steerable tube 450 may have any number, type, shape, and arrangement of cut-out features 461.

As mentioned above, the steerable tube 450 includes channels or grooves 470a-e configured to receive the conduits 400. The channels 470a-e may comprise indentations, grooves, or enclosed passageways. In the pictured embodiment, the steerable tube 450 includes five grooves 470a, 470b, 470c, 470d, and 470e that correspond to the conduits 400a, 400b, 400c, 400d, and 400e extending along the inner sheath 365. In the pictured embodiment, the grooves 470a-e have a generally hemispherical cross-sectional shape. In other embodiments, the grooves 470a-e may have any of a variety of cross-sectional shapes, including, by way of non-limiting example, a complete or closed circle, an incomplete or partial circle, an incomplete or partial polygon, or a complete or closed polygon. In some embodiments, the grooves 470a-e may have an open cross-sectional shape. In other embodiments, the grooves 470a-e may have a closed cross-sectional shape. In some embodiments, where the conduits 400 are arranged in a particular radial pattern relative to a longitudinal axis of the proximal portion 330 of the flexible body 216, the grooves 470 are arranged in the same radial pattern relative to the longitudinal axis AA of the steerable tube 450 such that the conduits 400 maintain the same radial pattern from the proximal portion 220 to the distal portion 331 of the flexible body 332.

The grooves 470a, 470b, 470c, 470d, and 470e are disposed circumferentially around the steerable tube 450 on the inner surface 452 of the steerable tube. The circumferential position of the grooves 470a-e on the steerable tube 450 correlate with the circumferential position of the conduits 400 on the inner sheath 365, and are generally parallel to the longitudinal axis AA of the steerable tube 450. Thus, the conduits 400 (or tendons if the conduits have been proximally terminated) may be slidably received within the grooves 470 of the steerable tube 450 without terminating or kinking the conduits 400. This configuration allows for the conduits 400 to extend alongside the steerable tube 450 while maximizing the potential inner diameter D1 of the lumen 334, minimizing the outer diameter D2 of the distal portion 331 of the flexible body, and maximizing the wall thickness of the steerable tube 450.

As shown in FIG. 6a, the grooves 470 extend from the proximal end 500 to the distal end 505 on the inner surface 452. The grooves 470 extend in a substantially straight path in parallel with the longitudinal axis AA of the steerable tube 450. In other embodiments, the grooves 470 may form a non-straight (e.g., curved or spiral) path within the steerable tube 450.

In some embodiments, the grooves 470 are intelligently aligned relative to the cut-out features 461 of the steerable tube 450 to maximize the mechanical performance of the steerable tube 450. In particular, the grooves 470 may be disposed on the steerable tube 450 such that the grooves 470 are rotationally shifted away from the generally axial-webs of tube material (i.e., the "struts" of the steerable tube 450). As shown in FIG. 6a (and similarly in the embodiment shown in FIG. 8), the grooves 470 extend or cut through the "rings" of the steerable tube 450, but avoid the "struts" of the steerable tube 450. This arrangement provides maximum steerable tube material for supporting axial compression. If the steerable tube 450 was weakest in torsion, however, the grooves 470 may shifted elsewhere relative to the "struts" on the steerable tube 450. In other words, the arrangement of the grooves 470 may be selected to avoid cutting the weakest part of the steerable tube 450 or flexure with the grooves 470.

As shown in FIGS. 6a and 6b, the thickness 12 of the steerable tube 450 may be substantially uniform in the areas without the grooves 470, and the wall thickness may decrease by a substantially uniform amount in the area of the grooves 470. The steerable tube 450 may have a substantially uniform wall thickness T3 in the area of the grooves 470. The wall thickness T3 is less than the wall thickness T2. In some embodiments, the thickness T2 will range from 0.25 to 0.38 mm. In some embodiments, the thickness T3 will range from 0.07 to 0.127 mm. These measurements are presented for exemplary purposes only, and are not intended to be limiting. Other wall thicknesses are contemplated.

The steerable tube 450 may be made of any suitable biocompatible material that provides the requisite tensile and flexural properties. Suitable materials may include, by way of non-limiting example, shape memory material such as Nitinol, stainless steel, and plastics. In some embodiments, the steerable tube 450 is made from the same material throughout (e.g., Nitinol from the proximal end 500 to the distal end 505). In other embodiments, the steerable tube 450 may be made from two or more different materials (e.g., stainless steel in a less flexible zone and Nitinol in a more flexible zone).

One technique for the construction of the steerable tube 450 is laser cutting technology, which may produce the steerable tube 450 in an automatic fashion (e.g., by computer numeric controlled cutting). Fine changes in the wall thickness (e.g., T2 and T3), the length L, an inner diameter D1, and an outer diameter D2 may be automatically programmed and generated using laser cutting technology. Other suitable manufacturing methods may include, by way of non-limiting example, water jet cutting, electrochemical etching, electrical discharge machining, and diamond cutting. In some embodiments, the creation of the cut-out features 461 and the grooves 470 is followed by a suitable surface treatment, such as, by way of non-limiting example, etching or electro-polishing to deburr irregular surfaces or blunt sharp edges.

Figure 7:
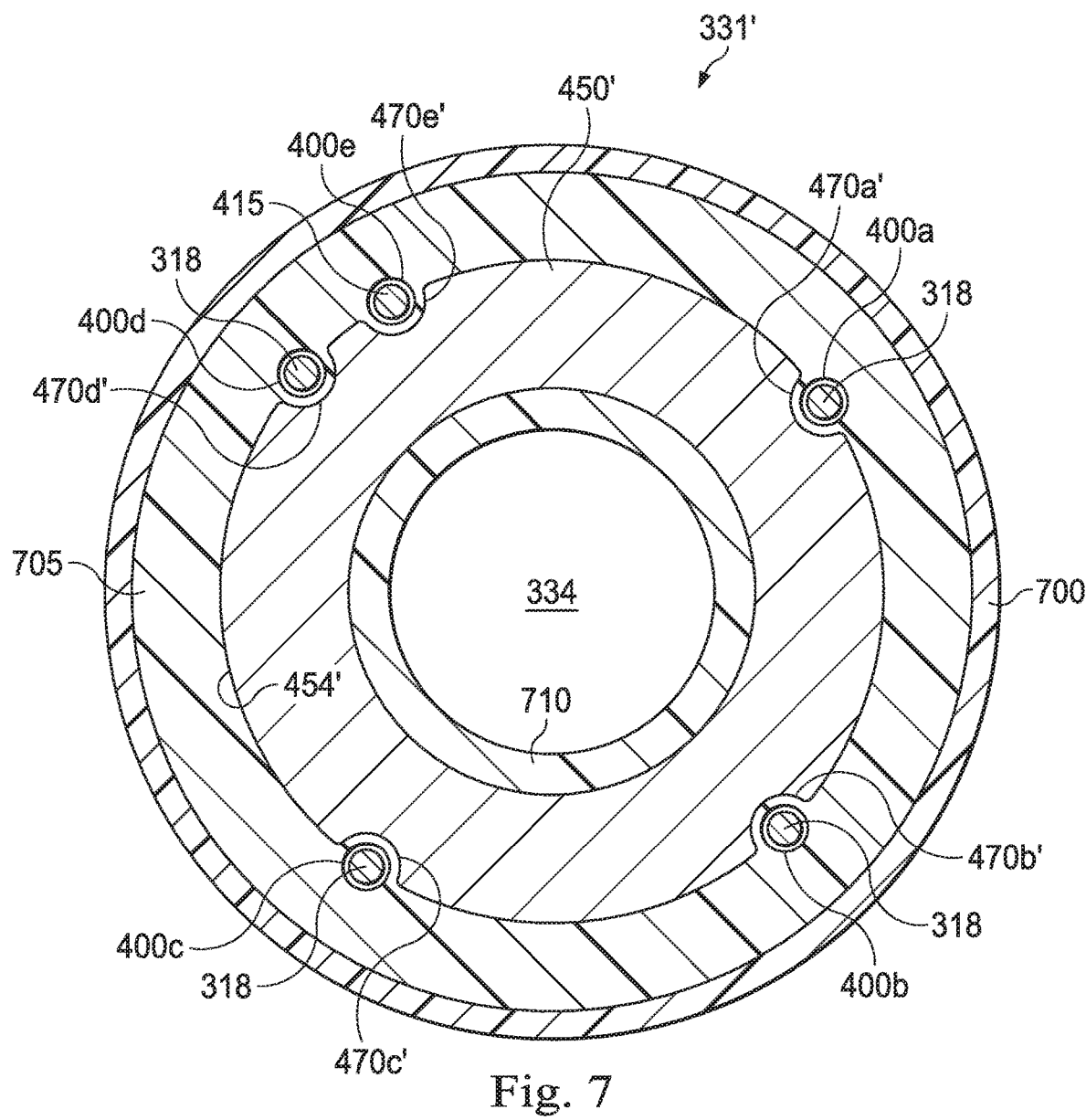
FIG. 7 illustrates a cross-sectional view of an exemplary distal portion of the instrument system pictured in FIG. 2.
Figure 8:
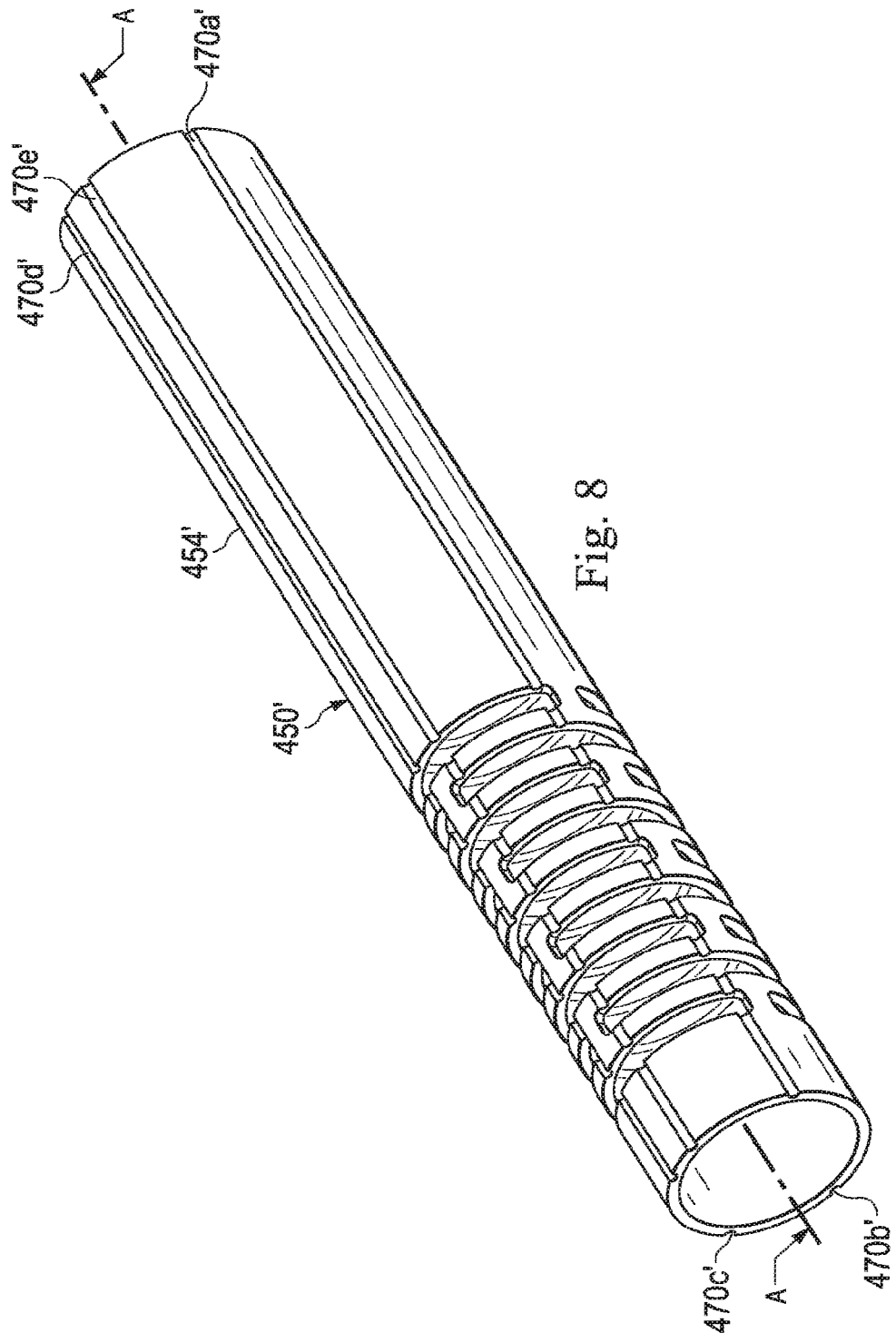
FIG. 8 illustrates a perspective view of an exemplary steerable tube according to one embodiment of the present disclosure.

In some embodiments, as shown in FIGS. 7 and 8, grooves 470a'-e' may be formed on the outer surface 454' of the steerable tube. FIG. 7 illustrates a cross-sectional view of an exemplary distal portion 331' of the exemplary instrument system. At the distal portion 331', the flexible body comprises a multi-layered, hollow cylindrical tube defining the lumen 334. In the pictured embodiment, the distal portion 331' comprises the outer sheath 700, a steerable tube 450', an inner sheath 705, and a luminal sheath 710, each of which is disposed concentrically and co-axially about the lumen 334. In some embodiments, the outer sheath 700 is substantially the same as the outer sheath 440 described above in relation to FIG. 5. In some embodiments, the inner sheath 705 is substantially the same as the inner sheath 365 described above in relation to FIGS. 4 and 5. In the pictured embodiment, the outer sheath 700 encases the inner sheath 705, the inner sheath 705 encases the steerable tube 450', and the steerable tube 450' concentrically surrounds the luminal sheath 710, which defines the lumen 334. Some embodiments may lack the luminal sheath 710.

As described above in relation to the inner sheath 365 shown in FIGS. 4-6b, the inner sheath 705 includes the five conduits, including the four tendon conduits 400a, 400b, 400c, and 400d configured to carry the tendons 318, and the sensor conduit 400e configured to carry the sensor element 415. The steerable tube 450' comprises a tubular member disposed between the inner sheath 705 and the luminal sheath 710. The steerable tube 450' is shaped and configured to carry the conduits 400 within indentations or grooves 470', which are described further below.

FIG. 8 illustrates a perspective view of the steerable tube 450' according to one embodiment of the present disclosure. The steerable tube 450' is substantially similar to the steerable tube 450 described above with reference to FIGS. 5-6b except for the differences described herein. The steerable tube 450' includes indentations or grooves 470' configured to receive the conduits 400. The grooves 470' are substantially similar to the groove 470 described above with reference to FIGS. 5-6b except for the differences described herein. In the pictured embodiment in FIGS. 7 and 8, the steerable tube 450' includes five grooves 470a', 470b', 470c', 470d', and 470e' that correspond to the conduits 400a, 400b, 400c, 400d, and 400e of the inner sheath 705. In the pictured embodiment, the grooves 470' are disposed on an outer surface 454' of the steerable tube 450'. In particular, the grooves 470a', 470b', 470c', 470d', and 470e' are disposed circumferentially around the steerable tube 450' on the outer surface 454' of the steerable tube. The circumferential position of the grooves 470' on the steerable tube 450' correlate with the circumferential position of the conduits 400 on the inner sheath 705. Thus, the conduits 400 of the inner sheath 705 may be slidably received within the grooves 470' of the steerable tube 450'. This configuration allows for the conduits 400 to extend alongside the steerable tube 450' while minimizing an outer diameter D2' of the distal portion 331 of the flexible body 216.

As shown in FIG. 8, the grooves 470' extend from the proximal end 500' to the distal end 505' on the outer surface 454'. The grooves 470' extend in a substantially straight path coaxially with the longitudinal axis AA of the steerable tube 450'. In other embodiments, the grooves 470' may form a non-straight (e.g., curved or spiral) path within the steerable tube 450'.

Figure 9:
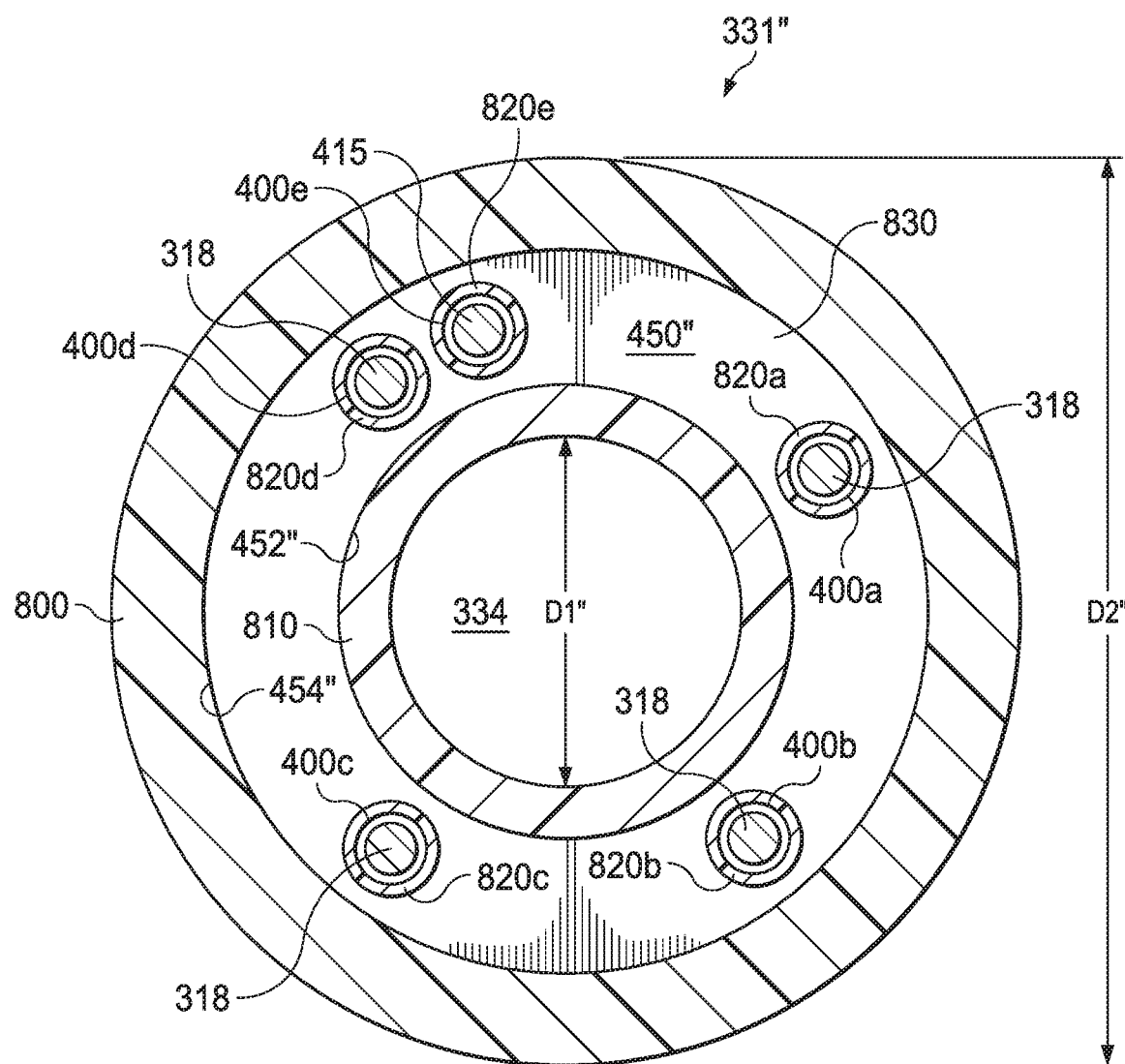
FIG. 9 illustrates a cross-sectional view of an exemplary distal portion of the instrument system pictured in FIG. 2.

In some embodiments, the grooves 470 may be formed within the wall of the steerable tube 450 between the inner surface 452 and the outer surface 454 of the steerable tube 450. For example, FIG. 9 illustrates a cross-sectional view of an exemplary distal portion 331" of the exemplary instrument system 200 pictured in FIG. 2. At the distal portion 331", the flexible body 216" of the instrument system 200 comprises a multi-layered, hollow cylindrical tube defining the lumen 334. In the pictured embodiment, the flexible body 332" comprises the outer sheath 800, a steerable tube 450", and a luminal sheath 810, each of which is disposed concentrically and co-axially about the lumen 334. In some embodiments, the outer sheath 800 is substantially the same as the outer sheath 440 described above in relation to FIG. 5. In some embodiments, the luminal sheath 810 is substantially the same as the luminal sheath 710 described above in relation to FIG. 7. In the pictured embodiment, the outer sheath 800 encases the steerable tube 450", and the steerable tube 450" concentrically surrounds the luminal sheath 810, which defines the lumen 334. Some embodiments may lack the luminal sheath 810.

The steerable tube 450" is substantially similar to the steerable tube 450 described above with reference to FIGS. 5-6b except for the differences described herein. The steerable tube 450" includes channels 820 configured to receive the conduits 400. In the pictured embodiment, the steerable tube 450" includes five channels 820a, 820b, 820c, 820d, and 820e that correspond to the conduits 400a, 400b, 400c, 400d, and 400e. In the pictured embodiment, the channels 820 comprise enclosed cylindrical passageways that are disposed within a wall 830 of the steerable tube 450" between an inner surface 452" and an outer surface 454" of the steerable tube 450". In particular, the channels 820a, 820b, 820c, 820d, and 820e are disposed circumferentially around the steerable tube 450" within the wall 830 of the steerable tube 450". The circumferential position of the channels 820 on the steerable tube 450" correlate with the circumferential position of the conduits 400 on an inner sheath 365 within the proximal portion 330 of the flexible body 332 (e.g., as shown in FIG. 4). Thus, the conduits 400 of the inner sheath 365 may be slidably received within the channels 820 of the steerable tube 450". This configuration allows for the conduits 400 to extend within the steerable tube 450" while minimizing an outer diameter D2" of the distal portion 331" of the flexible body 332" and maximizing an inner diameter D1" of the flexible body 332'.

Figure 10:
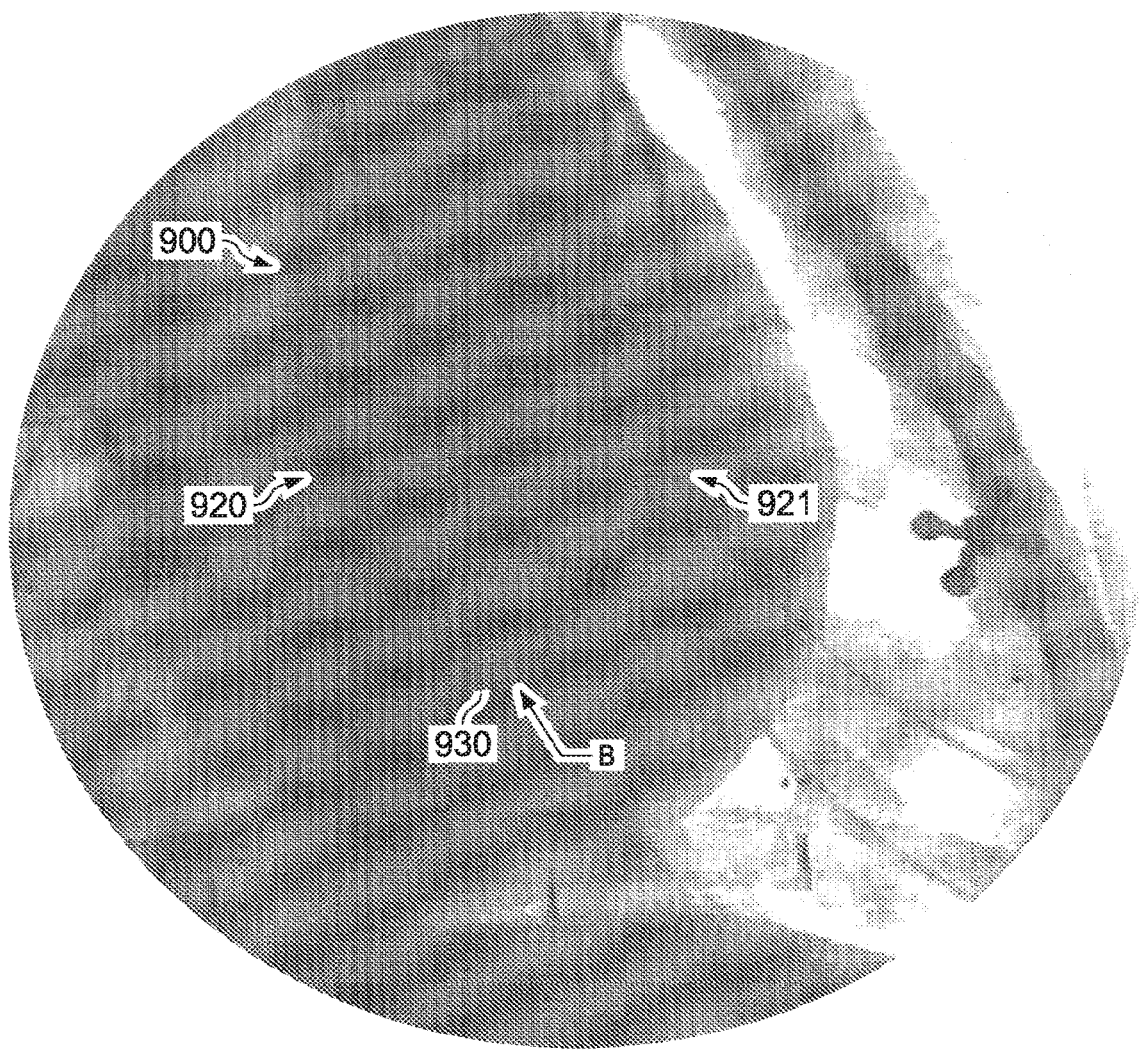
FIG. 10 illustrates an exemplary radiographic image of a nonexemplary instrument system navigating a turn within a tubular structure.

FIG. 10 illustrates an exemplary radiographic image of a flexible body 900 navigating a turn within an exemplary anatomic structure. The flexible body 900 lacks the embedded conduits 400 and the steerable tube 450 disclosed in FIGS. 3-9. In the flexible body 900, the conduits (e.g., coil pipes) that carry the control tendons 318 may be anchored to the flexible body 900 at a discrete element (e.g., a rigid ring) disposed between a proximal portion 920 and a distal portion 921 of the flexible body 900 at a transition 930. When the flexible body 900 curves, the flexible body 900 displays a sharp bend at the transition 930 between the proximal portion 920 and the distal portion 921 of the flexible body 900, as indicated by the arrow B. A sharp bend can cause a shape sensor component to malfunction and can limit steering control by kinking or constraining steering cables. Such a sharp bend may also hamper the clinician's ability to retract the flexible body.

Figure 11:
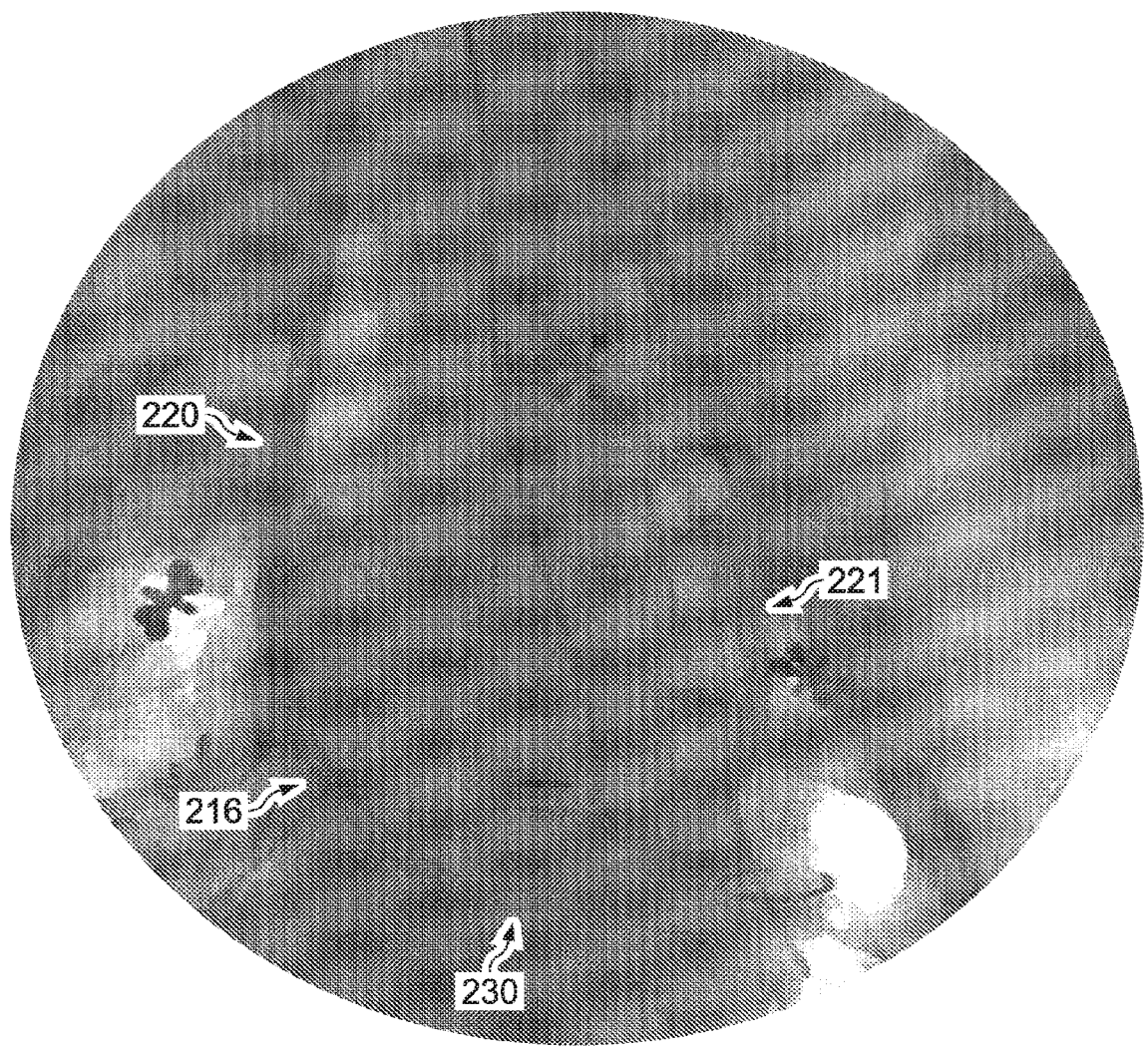
FIG. 11 illustrates an exemplary radiographic image of an exemplary instrument system navigating a turn within a tubular structure, where the exemplary instrument system incorporates embedded conduits and a steerable tube in accordance with the principles of the present disclosure.

FIG. 11 illustrates an exemplary radiographic image of the flexible body 216, incorporating the embedded conduits 400 and, optionally, the steerable tube 450 in accordance with the principles of the present disclosure. As described above in relation to FIGS. 2 and 4, the conduits 400 are embedded or otherwise housed within the inner sheath 365 along the entire length of the conduits 400. In the pictured embodiment, the inner sheath 365 365 (not shown in FIG. 11) extends continuously along the length of the flexible body 216, from the proximal portion 220 to the distal portion 221, and extends alongside or within the steerable tube 450. Instead of being fixedly attached to a rigid anchor element (e.g., a rigid ring) at a transition section 230, a conduit termination location, or other anchoring location, the conduits 400 extend continuously through and terminate within the wall of the flexible body 216. In some embodiments, the conduits 400 (not shown in FIG. 11) extend continuously within the inner sheath 365, which may extend through the transition 230 from the proximal portion 220 to the distal portion 221 of the flexible body 216 (shown in FIG. 2). In some embodiments, the inner sheath 365 extends only through the transition 230. In other embodiments, the conduits 400 and/or the inner sheath 365 terminate at the distal end of the flexible body 216.

As shown in FIG. 11, the embedded conduits 400 (and the consequent lack of a rigid anchor element at the transition 230) enable the flexible body 216 to curve gradually as the flexible body 216 navigates the anatomical turn, instead of experiencing an abrupt bend (e.g., at a rigid anchor element) as illustrated in FIG. 10. 'thus, the flexible body 216 remains flexible at the transition 230 while still maintaining articulation that may be isolated to the distal portion 221. The embedded conduits 400 and grooved steerable tube 450 allows for the flexible body 216 to maintain a continuous, uninterrupted curve from the proximal portion 220 through the distal portion 221. The ability of the flexible body 216 to bend as a continuous curve without kinking facilitates more efficient and safer navigation through the anatomy. In particular, the possibility of inadvertently puncturing or otherwise injuring the surrounding anatomy (e.g., due to force applied at a sharply bent or kinked transition 230) during advancement of the flexible body 216 is lessened because the flexible body 216 (having the conduits 400 embedded in the inner sheath 365 through the transition 230) can more easily curve and approximate the natural anatomical pathways than flexible bodies having rigid anchor elements at the transition 230 for the conduits 400.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A minimally invasive medical instrument comprising:
    an elongate flexible body comprising:
        a proximal portion;
        a distal portion;
        a transition portion between the proximal portion and the distal portion;
        an inner sheath extending at least within the proximal portion, the inner sheath comprising a plurality of conduits extending through a wall of the inner sheath, wherein a distal end of each conduit terminates at the transition portion; and
        a steerable tube extending within the distal portion, the steerable tube comprising a plurality of grooves in a wall of the steerable tube; and
    at least one tendon extending from the proximal portion into the distal portion of the elongate flexible body,
    wherein in the proximal portion, the at least one tendon extends through at least one conduit of the plurality of conduits, and wherein in the distal portion, the at least one tendon extends within at least one groove of the plurality of grooves.

2. The minimally invasive medical instrument of claim 1, wherein the inner sheath further comprises a plurality of protrusions extending at least within the proximal portion.

3. The minimally invasive medical instrument of claim 2, wherein each protrusion of the plurality of protrusions surrounds a portion of a corresponding conduit of the plurality of conduits.

4. The minimally invasive medical instrument of claim 1, wherein an outer diameter of the proximal portion is larger than an outer diameter of the distal portion.

5. The minimally invasive medical instrument of claim 1, wherein the elongate flexible body further comprises:
    an outer sheath; and
    a support component positioned between the inner sheath and the outer sheath.

6. The minimally invasive medical instrument of claim 5, wherein the support component comprises a tubular braided element.

7. The minimally invasive medical instrument of claim 1, wherein each of the conduits of the plurality of conduits includes a conduit lumen, and wherein at least one of the plurality of conduits houses a sensor element within its conduit lumen.

8. The minimally invasive medical instrument of claim 1, wherein a proximal end of each conduit is fixed relative to an actuator, and wherein the distal end of each conduit is fixed to the inner sheath in the transition portion.

9. The minimally invasive medical instrument of claim 1, wherein a proximal end of each tendon is fixed relative to an actuator, and wherein a distal end of each tendon is fixed to the distal portion.

10. The minimally invasive medical instrument of claim 1, wherein the plurality of conduits are oriented substantially parallel to a longitudinal axis of the elongate flexible body.

11. The minimally invasive medical instrument of claim 1, wherein the plurality of conduits are oriented in a curved pattern relative to a longitudinal axis of the elongate flexible body.

12. The minimally invasive medical instrument of claim 1, wherein each groove of the plurality of grooves is formed on an outer surface of the wall of the steerable tube.

13. A minimally invasive medical system comprising:
    an actuator;
    an elongate flexible body comprising:
        a proximal portion;
        a distal portion;
        a transition portion between the proximal portion and the distal portion;
        an inner sheath extending at least within the proximal portion; and
        a steerable tube extending within the distal portion, the steerable tube comprising a plurality of grooves in a wall of the steerable tube;
    a plurality of conduits extending through a wall of the inner sheath, wherein a distal end of each conduit terminates at the transition portion; and
    a plurality of actuation tendons extending from the proximal portion into the distal portion of the elongate flexible body,
    wherein in the proximal portion, each actuation tendon extends through a corresponding conduit of the plurality of conduits, wherein in the distal portion, each actuation tendon extends within a corresponding groove of the plurality of grooves, and wherein the plurality of actuation tendons are actuatable by the actuator to bend the distal portion.

14. The minimally invasive medical system of claim 13, wherein the inner sheath comprises a plurality of protrusions extending at least within the proximal portion.

15. The minimally invasive medical system of claim 14, wherein each protrusion of the plurality of protrusions surrounds a portion of a corresponding conduit of the plurality of conduits.

16. The minimally invasive medical system of claim 13, wherein an outer diameter of the proximal portion is larger than an outer diameter of the distal portion.

17. The minimally invasive medical system of claim 13, further comprising a support component positioned between the inner sheath and an outer sheath of the elongate flexible body.

18. The minimally invasive medical system of claim 17, wherein the support component comprises a tubular braided element.

19. The minimally invasive medical system of claim 13, wherein the plurality of actuation tendons are actuatable to bend the steerable tube.

20. The minimally invasive medical system of claim 13, wherein each groove of the plurality of grooves is formed on an outer surface of the wall of the steerable tube.

\* \* \* \* \*